US00PP14321P39

(12) United States Plant Patent
Southwick

(10) Patent No.: US PP14,321 P3
(45) Date of Patent: Nov. 25, 2003

(54) MAHALEB ROOTSTOCK NAMED 'UCMH 55'

(50) Latin Name: *Prunus mahaleb*
Varietal Denomination: UCMH 55

(75) Inventor: Stephen M. Southwick, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 17 days.

(21) Appl. No.: 10/028,771

(22) Filed: Dec. 28, 2001

(65) Prior Publication Data

US 2003/0126662 P1 Jul. 3, 2003

(51) Int. Cl.[7] ..... A01H 5/00

(52) U.S. Cl. ..... Plt./183
(58) Field of Search ..... Plt./183, 180

*Primary Examiner*—Anne Marie Grunberg
(74) *Attorney, Agent, or Firm*—Burns, Doane, Swecker & Mathis, L.L.P.

(57) ABSTRACT

A new and distinct cultivar of *Prunus mahaleb* is provided. The new cultivar is particularly well suited for serving as an understock during cherry production. A number of advantages are provided when compared to the standard Mahaleb rootstock. The cultivar is readily amenable to vegetative propagation (e.g., by the use of softwood cuttings), and exhibits improved resistance to Phytophthora spp. When used with a 'Bing' cherry scion, increased yields have been observed. The new cultivar when grown without use as an understock forms a tree that is intermediate in size and forms more fine wood when compared to the 'UCMH 56' and 'UCMH 59' cultivars that were products of the same research program.

5 Drawing Sheets

Botanical/commercial classification: *Prunus mahaleb*/ Mahaleb Rootstock.
Varietal denomination: cv. 'UCMH 55'.

SUMMARY OF THE INVENTION

Mahaleb rootstocks (i.e., *Prunus mahaleb* rootstocks) are widely used during both sweet and sour cherry production throughout the world. It has been the common practice to form such rootstock plants from seed following the random outcrossing of parent plants. Accordingly, cherry production encountered when using such plants as an understock has tended to be somewhat variable due to differences in the genotype of the understock. Such variation often has led to reduced field performance on some cherry trees on a random and unpredictable basis. Mahaleb rootstocks in the past have generally been found to be incapable of vegetative propagation on a reliable basis, such as through the use of softwood and hardwood cuttings. Also, such rootstocks in the past have been susceptible to root and crown fungal diseases generally known as Phytophthora spp.

SUMMARY OF THE NEW CULTIVAR

It was an object of my research to provide *Prunus mahaleb* rootstocks that possess characteristics that overcome shortcomings of the Mahaleb rootstock presently being used during cherry production. More specifically, it was my goal to provide cherry rootstocks that could be vegetatively propagated in an expeditious and reliable manner so that cherry growers can eliminate crop variation that can be traced to lack of uniformity in the rootstock. Also, it was a goal of my research to provide new Mahaleb rootstocks that inherently display needed resistance to disease and thereby make possible a satisfactory cherry crop on a more consistent basis combined with a reduction in the need to replant because of tree loss that is traceable to disease.

The original tree of the new *Prunus mahaleb* cultivar of the present invention was discovered through detailed evaluation and selection while growing in a cultivated area at the Experimental Orchards at the University of California located at Davis, Calif., U.S.A. The exact parentage of the new cultivar is unknown. The seeds used to form the planting where the discovery took place came from a random collection of wild *Prunus mahaleb* germplasm that had been collected from around the world. The large number of seedlings present in the planting were carefully studied and evaluated and a single plant possessing the combination of characteristics of the new cultivar of the present invention was selected and was preserved. Accordingly, the plant of the new cultivar was produced by the hand of man and was not found while growing in the wild. Had this plant not been discovered and preserved, it would have been lost to mankind.

Other *Prunus mahaleb* cultivars resulting from the same research are 'UCMH 56' (U.S. Plant patent application Ser. No. 10/028,772, filed concurrently herewith), and 'UCMH 59' (U.S. Plant patent application Ser. No. 10/029,284, filed concurrently herewith).

It was found that the new *Prunus mahaleb* cultivar of the present invention exhibits the following combination of characteristics:

(a) readily is amenable to vegetative propagation, (b) performs well as an understock for cherry production, (c) forms a tree that is intermediate in size and forms more fine wood when compared to the 'UCMH 56' and 'UCMH 59' cultivars, and (d) displays improved resistance to Phytophthora spp.

In view of the above combination of characteristics, the new cultivar of the present invention well meets the needs of cherry producers for use as an improved rootstock. Cherry scion characteristics are no longer influenced by variation in the Mahaleb rootstock resulting from the random outcrossing of parental plants. Also, the disease resistance made possible by the new cultivar is a major advantage for cherry producers.

The new cultivar of the present invention has been repeatedly reproduced through the use of softwood and hardwood cuttings at Davis, Calif., U.S.A. Such propagation has confirmed that the characteristics of the new cultivar are stable and are firmly fixed and are transmitted to subsequent generations on a reliable basis.

The new cultivar of the present invention initially was designated 'UC Mahaleb 155-1', and subsequently has been named 'UCMH 55'.

BRIEF DESCRIPTION OF THE PHOTOGRAPHS

The accompanying photographs show specimens of the plant and plant parts, and also provide DNA information concerning the new cultivar of the present invention. Color is shown as nearly true as is possible to make the same in color illustrations of this character. The trees of the new cultivar were grown at the Experimental Orchards of the University of California located at Davis, Calif., U.S.A.

FIG. 1 shows a tree of approximately 5 to 7 years of age during December. The tree is a mother plant that was being used to make propagules for additional testing and evaluation. Most of the leaves had dropped by the end of the preceding October.

Figure 1:
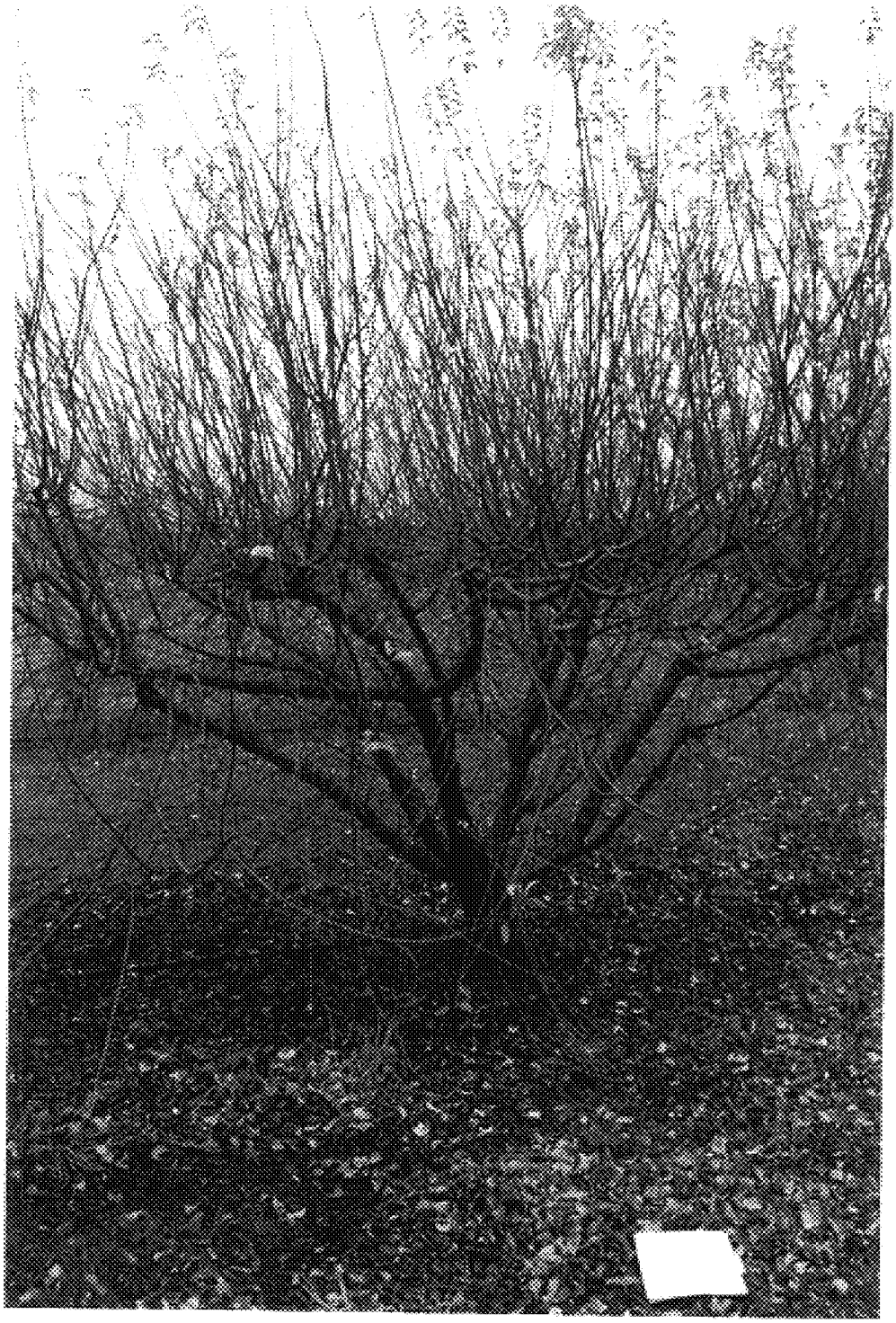
Figure 2:
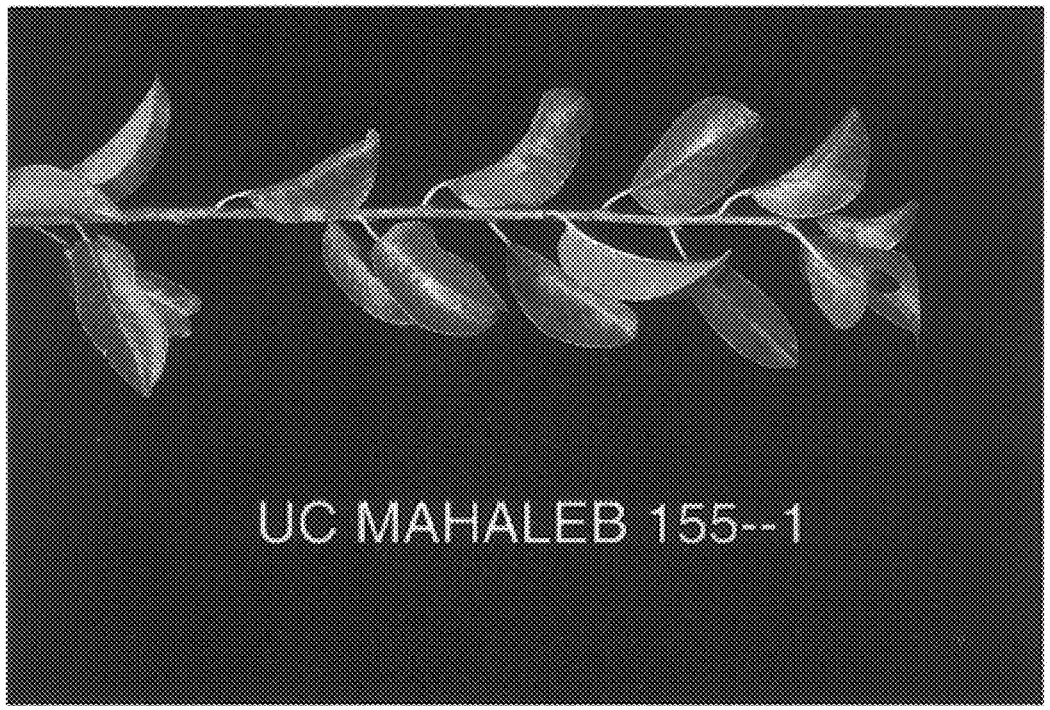
FIG. 2 shows a specimen of a current season's shoot with leaves collected during mid-October. Such shoot was suitable for use to make a hardwood or semi-hardwood cutting.
Figure 3:
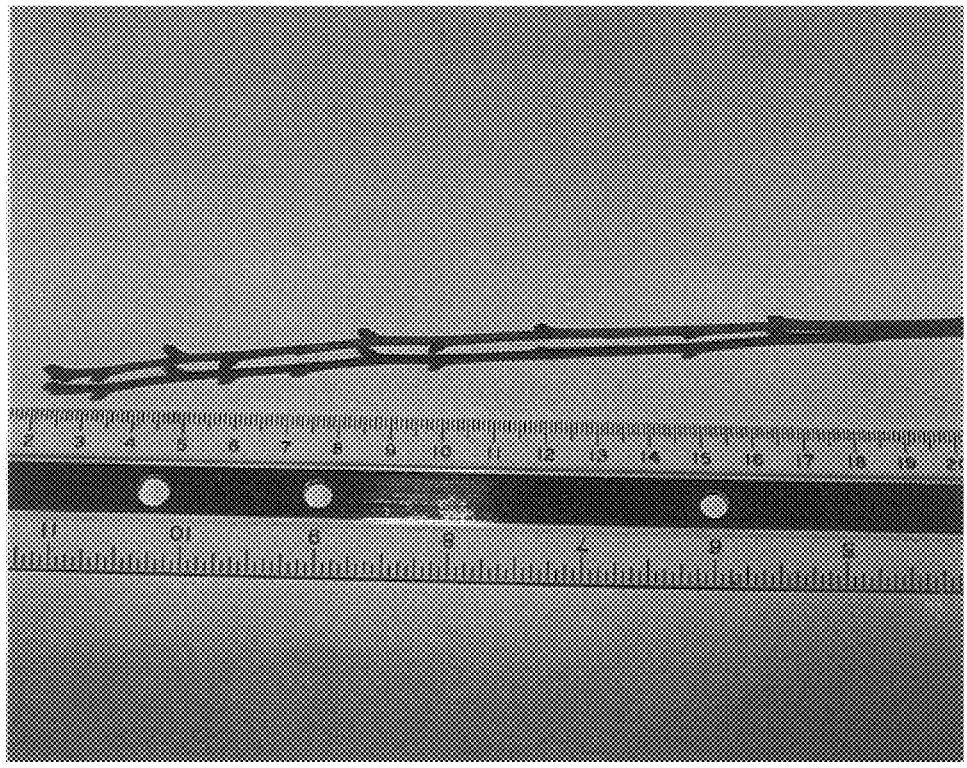
FIG. 3 shows a specimen of typical branch tip with buds of the new cultivar during the winter. Dimensions in centimeters and inches are included.
Figure 4:
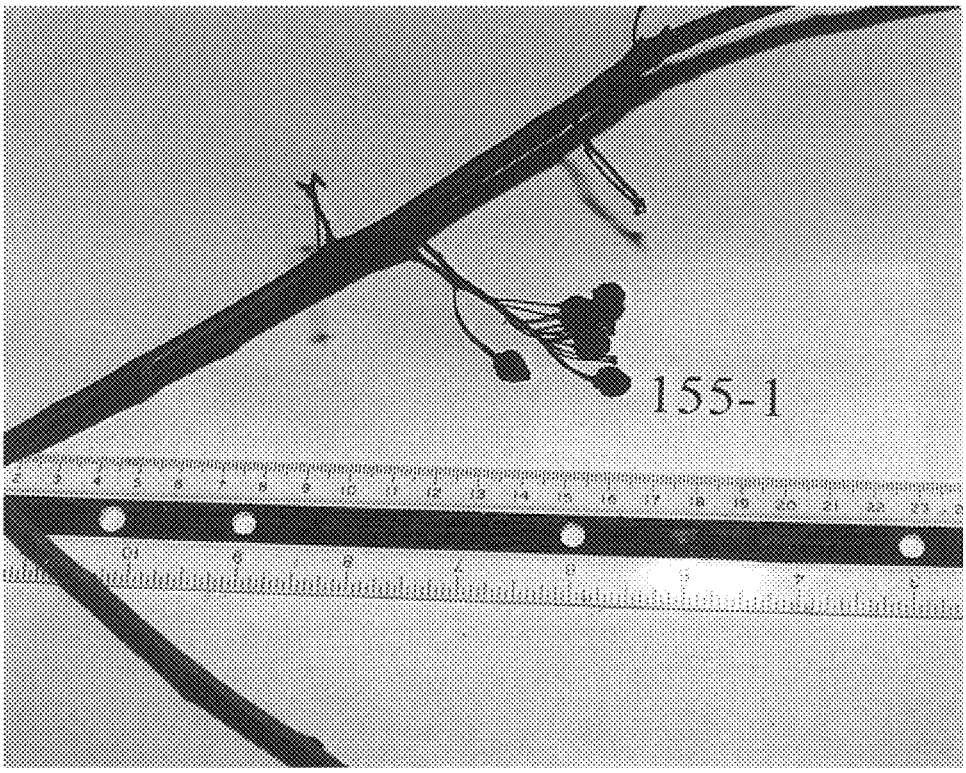
FIG. 4 shows specimens of typical branches with dried fruit of the new cultivar during the winter. Dimensions in centimeters and inches are included.
Figure 5:
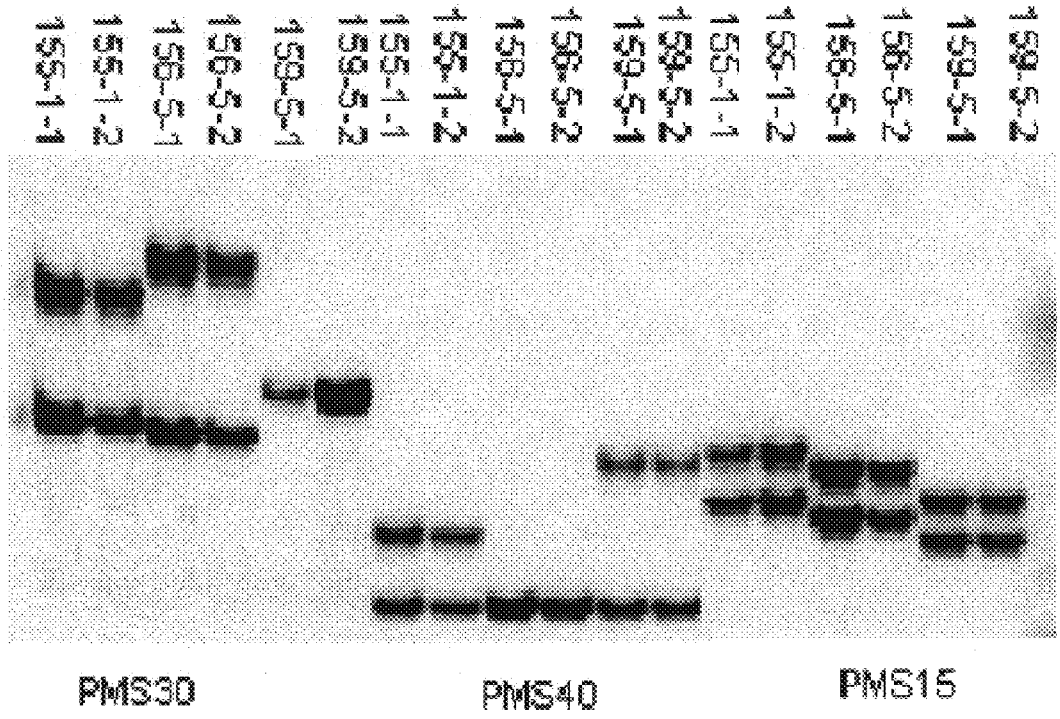

FIG. 5 shows the DNA fingerprint of the new cultivar of the present invention as well as that of the 'UCMH 56' and 'UCMH 59' cultivars for comparative purposes. Three microsatellite markers were used during the DNA determinations (i.e., PMS30, PMS40 and PMS15). Data with respect to the plants of the new cultivar of the present invention is designated "155-1". Data with respect to the plants of the 'UCMH 56' cultivar is designated "156-5", and data with respect to the 'UCMH 59' cultivar is designated "159-5".

Figure 6:
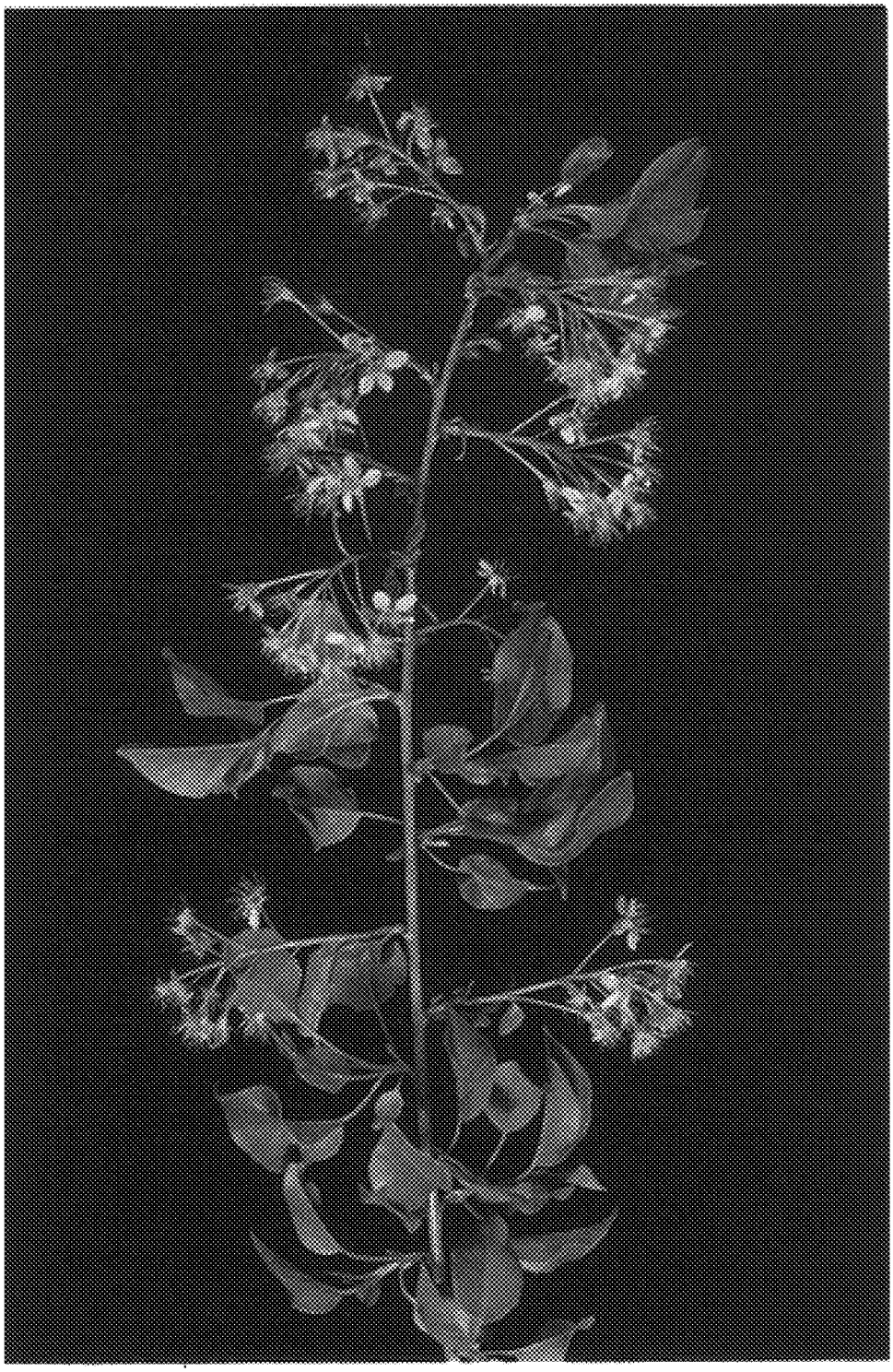

FIG. 6 shows typical inflorescences of the new cultivar.

The primer sequences (SEQ ID Nos.: 1–6) used in this determination are as follows:

```
PMS 30   Forward CTG TCG AAA TGC CTA TGC
         Reverse ATG AAT GCT GTG TAC ATG AGGC,
PMS 40   Forward TCA CTT TCG TCC ATT TTC CC
         Reverse TCA TTT TGG TCT TTG AGC TCG,
PMS 15   Forward TCC GCT TCT CTG TGA GTG TG
         and
         Reverse CGA TAG TTT CCT TCC CAG ACC.
```

When preparing the DNA fingerprints, a total of six leaf samples were randomly collected from two different but replicate trees. Accordingly, each genotype was sampled and replicated twice. The two samples are distinguished during the presentation of data by the final digit shown in FIG. 5 (i.e., by "−1" or by "−2"). DNA was extracted using Dneasy Plant Kit from Qiagene, Inc. (Valencia, Calif., U.S.A.) following the manufacturer's protocol. The extracted DNA was purified by adding 1/10 volume 3M sodium acetate and 2 volumes 100 percent ethanol and subsequent storage at −20° C. for an hour. The samples were centrifuged at 13,000 rpm for 15 minutes and the pellets were washed two times with 70 percent ethanol. The pellets were air dried and resolved in 50 $\mu$l TE buffer. Quantification of DNA was performed with ethidium bromide agarose gel plates. PCR was carried out under the following conditions: 100–150 ng of template DNA, 250 nM of each primer, 200 $\mu$M of dNTPs, 0.5 U of Taq Polymerase, and 1.5 mM of $MgCl_2$. The reaction was run for 45 cycles (denaturing at 94° C. for 1 minute, annealing at 60° C. for 1 minute, with a two minute extension at 72° C.), followed by a single extension at 72° C. for 60 minutes. The amplification products were detected on 5.5 percent polyacrylamide gels using a Li-Cor $IR^2$ 4200 DNA sequencer (Li-Cor, Nebraska, U.S.A.). The three microsatellite markers clearly distinguished the three cultivars. Both repeats of each rootstock showed identical fingerprints. The marker PMS30 produced two bands for rootstock 'UCHM 55' at 132bp (base pair) and 159bp, two bands for 'UCMH 56' at 132bp and 168bp, and one band for 'UCMH 59' at 142bp. Marker PMS40 produced two bands for 'UCMH 55' at 92bp and 111bp, and one band for 'UCMH 56' at 92bp, and two bands for 'UCMH 59' at 92bp and 129bp. Marker PMS15 produced two bands for 'UCMH 55' at 118bp and 128bp, two bands for 'UCMH 56' and 112bp and 123bp, and two bands for 'UCMH 59' at 105bp and 115bp.

FIG. 6 shows a typical inflorescence.

DETAILED DESCRIPTION

The following is a detailed description of the new cultivar. The tree was grown at the Experimental Orchards of the University of California at Davis, Calif., U.S.A. Color designations are presented with reference to the "Dictionary of Color" by Maerz and Paul, First Edition (1930).

Tree:

*Size.*—Intermediate to the 'UCMH 56' and 'UCMH 59' cultivars. An eight year-old tree of the 'UCMH 55' cultivar that has undergone some pruning commonly will display a height of approximately 4 meters and a width of approximately 3 meters. Trunk girth at 30 cm above the soil line commonly will possess a cross-sectional area of approximately 400 $cm^2$.

*Growth.*—Spreading, the upper canopy is very upright, and two-year-old wood in the lower canopy is pendulous. All wood is very fine. Forms more fine wood than the 'UCMH 56' and 'UCMH 59' cultivars.

*Bark.*—Possesses a rough raised surface and an Iron grey (24 A 2) coloration.

Branches:

*Shoot growth form.*—Straight with spirally-arranged leaves, (single at each node), laterals are highly branched and secondaries are mostly unbranched, and laterals arise at approximately 75 to 90 degrees from the point of origin on the main scaffold.

*Size.*—Both current and previous season wood is fine and commonly displays a diameter of less than 1 cm.

*Spurs.*—Commonly 9 to 16 spurs are present per 85 cm of previous season shoot that measure approximately 5 to 7 cm in length. The coloration is Chickadee gray (47 A 1) underlaid with Malaga (7 L 1).

*Internode length.*—Internodes of mixed shoots having a length of approximately 40 to 100 cm commonly vary in length from approximately 1.3 to 3.6 cm.

*Shoot bark.*—Smooth in texture, and the coloration is light brown with a silvery cast varying from Arabian night brown (14 A 11) to 14 G 8.

*Main scaffold bark.*—Platinum (45 A 3) in coloration with an underlay of Rubient (55 L 8).

*Lenticels.*—Prominent, densely distributed, and under magnification are raised. On the main scaffold and lower large limbs the coloration is Parchment (12 B 3). On the shoot bark the length commonly ranges from approximately 2.5 to 5 mm and the coloration is Iron grey (24 A 2). On the subsidiary branches the length commonly ranges from approximately 2 to 5 mm, the frequency is approximately 8 per square inch, and the coloration is Parchment (12 B 3).

*Axillary buds.*—Borne on spurs of varying length on previous season growth axillary, imbricate, sessile, and single. The bud tips are pointed and the bud pose is adpressed on dormant new wood. The bud support is small. Vegetative buds proximal to the reproductive portion of the shoot commonly are borne spirally.

Leaves:

*Bearing.*—Simple, spirally-arranged and petiolate.

*Pose.*—Curved outward and downward and often curl under slightly at the apex.

*Length.*—Approximately 5 to 6 cm in length excluding the petiole and approximately 3 to 4.5 cm in width on the upper canopy and on the lower canopy.

*Width.*—Approximately 3 to 4.5 cm on the upper canopy and on the lower canopy.

*Form.*—Oval-elliptic to oval with an acuminate tip and a truncate base on the upper canopy and on the lower canopy.

*Margins.*—Crenate and glandular between rounded teeth.

*Surfaces.*—Glabrous on the dorsal and ventral surfaces with short stiff hairs along the midrib of the ventral surface that are visible with magnification.

*Petiole.*—Commonly with glands that are dark Russet brown (14 I 12) at the leaf-petiole juncture, approximately 1.5 to 2 cm in length, and Russet green (20 K 1) in coloration on the upper canopy and on the lower canopy. Such glands commonly are less than 1 mm in length and less than 0.5 mm in width.

*Venation.*—Pinnate, with the midrib and other venation being Russet green (20 K 1) in coloration.

*Color.*—21 L 6 (Parrot Green) to 21 L 9 on the upper surface and Piquant green (20 K 6). on the under surface.

*Leaf drop.*—On Dec. 11, 2000 there was approximately 95 percent leaf fall.

*Bloom time.*—Full bloom on Mar. 29, 2002.

*Floral buds.*—Approximately 2 mm in length and approximately 1 mm in width, and Burmese ruby (7 H 6) in coloration.

Flowers:

*Type.*—Single or inflorescent in panicles.

*Form.*—The paniculate inflorescence commonly has approximately 8 to 14 flowers with a peduncle including rachis of approximately 2.5 to 4 cm in length and a pedicel of approximately 1.5 to 2 cm in length. Anthesis proceeds acropetally within the inflorescence. The paniculate inflorescence commonly bears one or two bracts at the base of or on the peduncle and a single bract at the base of the pedicel.

*Bearing.*—Inflorescences of approximately 8 to 14 flowers are borne spirally as well as single flowers on previous season laterals. Fruit bearing wood may be a 1 or 2 degree lateral, a mixed shoot in that the proximal portion (½ to ¾ of the shoot) is vegetative with axillary shoots that break after flowering, and with the distal portion of one year-old wood that bears single flowers or inflorescences directly on the fruit wood in the absence of spurs. The terminal bud is commonly a mixed vegetative bud (leaves and shoot).

*Pollination required.*—Any Mahaleb rootstock that is producing flowers which overlap with the bloom period.

*Color.*—White.

*Petal number.*—Five.

*Petal size.*—Approximately 6 mm in length and approximately 4 mm in width at the widest point.

*Sepals.*—Five.

*Carpel.*—Single with two ovules one of which commonly aborts.

*Pistil.*—Approximately 3.5 to 4 mm in length with the stigma and style being Marguerite Yellow (10 C 1) in coloration.

*Stamen.*—Commonly approximately 11 to 16 per flower, and approximately 6 to 7 mm in length.

*Anthers.*—Cossak green (23 L 11) in coloration when indehiscent.

*Filaments.*—Marguerite Yellow (10 C 1) in coloration.

*Pollen.*—Cossak green (23 L 11) in coloration.

*Scent.*—Mildly fragrant and similar to that of almond flowers.

Fruit:

*Chilling requirement.*—Approximately 750 to 1,000 hours less than or equal to 45° F.

*Bearing.*—Drupe.

*Maturity date.*—Late June to early July.

*Skin color.*—Dark purple-mahongany (56 A 12) to near back (48 A 12).

*Flesh color.*—Dark purple-mahogany (56 A 12) to near black (48 A 12).

*Flesh firmness.*—Soft when fully ripe and juicy.

*Cracking susceptibility.*—None observed during observations to date.

*Eating quality.*—Astringent and bitter taste renders unsuitable for eating.

*Shape.*—Oval and pointed at the pistillate end.

*Size.*—Approximately 1.5 to 2 cm in diameter.

*Juice color.*—Dark purple-mahogany (56 A 12) to near black (48 A 12).

*Fruit stalk.*—Short, approximately 1 to 1.8 cm. One or two very small bracts commonly persist at the base of the inflorescence. Such bracts are Paradise green (22 L 11) in coloration.

*Fruit drop.*—Susceptibility is high (approximately 50 to 100 percent).

*Stone shape.*—Substantially spherical.

*Stone size.*—Intermediate and approximately 7 to 8 mm in diameter.

*Seed color.*—Oyster white (10 B 1).

Disease resistance: The new cultivar has shown 100 percent survival rate in field trials at sites that are heavily infested with Phytophthora spp. and stem pitting virus. At the same sites, approximately 50 percent of the standard Mahaleb plants died.

Vegetative propagation: The new cultivar asexually reproduces well through the rooting of softwood and hardwood cuttings. The use of softwood cuttings is preferred.

Use as a scion rootstock: Field testing has been conducted using a scion of 'Bing' cherry following budding. Precocious flowering and cropping are facilitated when using the new cultivar as a rootstock. For instance, flower and fruit production can begin easily in the 4th or 5th growing season with the flowers opening earlier in the season. The fruit size has been found to be comparable to that formed with standard Mahaleb rootstock. To date the new cultivar produced low numbers of root and crown suckers.

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: PMS 30 forward primer

<400> SEQUENCE: 1

ctgtcgaaat gcctatgc                                                  18


<210> SEQ ID NO 2
<211> LENGTH: 22
<212> TYPE: DNA
<213> ORGANISM: Artificial Sequence
<220> FEATURE:
<223> OTHER INFORMATION: PMS 30 reverse primer

<400> SEQUENCE: 2

atgaatgctg tgtacatgag gc                                             22


<210> SEQ ID NO 3
<211> LENGTH: 20
<212> TYPE: DNA
<213> ORGANISM: Artificial Sequence
<220> FEATURE:
<223> OTHER INFORMATION: PMS 40 forward primer

<400> SEQUENCE: 3

tcactttcgt ccattttccc                                                20


<210> SEQ ID NO 4
<211> LENGTH: 21
<212> TYPE: DNA
<213> ORGANISM: Artificial Sequence
<220> FEATURE:
<223> OTHER INFORMATION: PMS 40 reverse primer

<400> SEQUENCE: 4

tcattttggt ctttgagctc g                                              21


<210> SEQ ID NO 5
<211> LENGTH: 20
<212> TYPE: DNA
<213> ORGANISM: Artificial Sequence
<220> FEATURE:
<223> OTHER INFORMATION: PMS 15 forward primer

<400> SEQUENCE: 5

tccgcttctc tgtgagtgtg                                                20


<210> SEQ ID NO 6
<211> LENGTH: 21
<212> TYPE: DNA
```

-continued

```
<213> ORGANISM: Artificial Sequence
<220> FEATURE:
<223> OTHER INFORMATION: PMS 15 reverse primer

<400> SEQUENCE: 6

cgatagtttc cttcccagac c                                              21
```

I claim:

1. A new and distinct cultivar of *Prunus mahaleb* plant that exhibits the following combination of characteristics:

(a) readily is amenable to vegetative propagation, (b) performs well as an understock for cherry production, (c) forms a tree that is intermediate in size and forms more fine wood when compared to the 'UCMH 56' and 'UCMH 59' cultivars, and (d) displays improved resistance to Phytophthora spp.;

substantially as illustrated and described.

* * * * *

Disclaimer & Dedication

PP. 14,321 P3 — Stephen M. Southwick, Davis, CA (US). MAHALEB ROOTSTOCK NAMED 'UCMH 56'. Patent dated Nov. 25, 2003. Disclaimer filed September 29, 2009, by the assignee, The Regents of the University of California.

Hereby disclaims and dedicates to the Public, all claims and the entire term of said patent.

(*Official Gazette, January 26, 2010*)